United States Patent [19]

Voegelé et al.

[11] 4,370,946

[45] Feb. 1, 1983

[54] METHOD FOR CONDITIONING AND PRESERVING EGGS OF INSECT OOPHAGE PARASITES OR PROCESS FOR CONDITIONING AND PRESERVATION OF EGGS OF OOPHAGOUS PARASITES OF INSECTS

[75] Inventors: Jean D. Voegelé; Pierre E. J. Jourdheuil, both of Antibes; Jeannine M. Pizzol nee Dalmasso, Parc des Mimosas; Bernard C. J. Pintureau, Antibes, all of France

[73] Assignee: Institut National de la Recherche Agronomique - UNRA, Paris, France

[21] Appl. No.: 243,962

[22] PCT Filed: Jul. 7, 1980

[86] PCT No.: PCT/FR80/00114

§ 371 Date: Mar. 6, 1981

§ 102(e) Date: Mar. 6, 1981

[87] PCT Pub. No.: WO81/00037

PCT Pub. Date: Jan. 22, 1981

[30] Foreign Application Priority Data

Jul. 9, 1979 [FR] France .............................. 79 17774

[51] Int. Cl.³ .............................................. A01K 67/00
[52] U.S. Cl. ............................................. 119/1; 119/15
[58] Field of Search ........................................ 119/1, 15

[56] References Cited

U.S. PATENT DOCUMENTS 3,893,420 7/1975 Andreev et al. ......................... 119/1
3,941,089 3/1976 Andreev et al. ......................... 119/1

Primary Examiner—Hugh R. Chamblee
Attorney, Agent, or Firm—Karl W. Flocks; Sheridan Neimark

[57] ABSTRACT

Process for conditioning and preservation of eggs of oophagous parasites of insects, intended particularly to the biological combat against certain depredators of plants. According to this process, starting initially with eggs of lepidoptera of foodstuffs, particularly *Iphestia Kuhniella*, which have been previously conditioned, these eggs are then parasited by adults of Trichogrammidae, the parasited eggs are submitted to an incubation period, the incubated eggs are submitted to an induction period, and then the eggs thus obtained are cold-preserved. Application particularly to the biological combat against the pyralis of the *Ostrinia nubilalis* hubner corn.

8 Claims, 3 Drawing Figures

METHOD FOR CONDITIONING AND PRESERVING EGGS OF INSECT OOPHAGE PARASITES OR PROCESS FOR CONDITIONING AND PRESERVATION OF EGGS OF OOPHAGOUS PARASITES OF INSECTS

BACKGROUND OF THE INVENTION

The present invention relates to a method for conditioning and preserving eggs of insect oophage parasites. In the field of agriculture, more particularly that of the protection of plants against damaging insects, by the biological route, it is known to resort to oophage parasites of the Trichogramma genus in the control of pests. For these pests, the method of control consists of mass-producing Trichogramma from eggs of a user host, generally selected from among Lepidoptera of food products, then of transferring these eggs, once parasitised, into the fields where they give birth to adult Trichogramma which parasite the eggs of the pests to be destroyed.

PRIOR ART

One of the limits in this method of biological control resides in the difficulty of storing the daily production of the Entomophage and of preserving it. In addition, it is known that the Trichogramma have in nature a hibernal arrest in development in their host eggs which permits them to pass several months in the state of suspended animation, either by simple quiescence, or by diapause. Certain authors such as ZORIN (1927) and TELENGA (1954-1956) have shown besides that it was necessary, for maintaining all the biotic potentialities of the parasite, to put it into the diapause state.

However, inspite of studies devoted to the diapause of the Trichogramma (see the works of TELENGA 1956, MASLENNEKOVA - TSYBUS'SKAYA - KAPUSTINA 1974), it is not possible at the present time (see in particular the works of CHERKASOV of 1976) to preserve Trichogramma in Winter which would remain active in the Spring. The studies of CHERKASOV have however enabled a method of preserving Trichogramma to be contemplated which proceeds in the following manner: one day's eggs of Noctuella Hadena sordida or of Aleucita of Sitotroga cerealella cereals were parasitised in the proportion of one parasite per 5 eggs at 23°-25° C., 70-80% relative humidity and a photoperiod of 16 hours for 3 days. These eggs were then placed at 10° C. with a photoperiod of 12 hours and a relative humidity of 70-80% until darkening of the eggs. At this stage, these eggs were preserved at 3° C. and at a relative humidity of 70-80%. This method enables, after 250 days of preservation, the obtaining of 36 to 48% of emergence of parasites. The fertility of the latter is reduced, in the neighbourhood of 20 eggs per female and the "sex-ratio" is in the favour of the males. The drawbacks of this production method for Trichogramma with reduced fertility, with a high percentage of males and of brachiptera with longevity reduced to two or three days, do not permit the use of such Trichogramma for release in the fields.

It is an object of the present invention to overcome these drawbacks and to provide a method of conditioning and preserving Trichogramma by cold, so that it is possible at any moment, from batches of these Entomophages stored from 3 to 12 months, to take specimens of parasitised eggs which give a hatching ratio, a fertility, a longevity, a percentage of winged individuals and a sex-ratio little different from those of unstored individuals.

Two variations of the method according to the invention enable respectively the obtaining of long storage, that is to say from 3 to 12 months, and short storage, that is to say up to about 45 days.

GENERAL DESCRIPTION OF THE INVENTION

The method according to the invention is essentially characterised by the fact that starting from eggs of Lepidoptera of food products, in particular from Ephestia Kuhniella, which have undergone a prior conditioning, these eggs are parasitised by Trichogramma adults, the so-parasitised eggs are subjected to an incubation period of at least 24 hours at 20° C., with a photoperiod of 8 hours of light and 16 hours of darkness and a relative humidity of 70 to 80%, that the eggs so-incubated are subjected to an induction period of about 6 to 80 days, at a temperature below 15° C., with a photoperiod of 8 hours of light and 16 h of darkness, and a relative humidity of about 70%, then that the eggs thus obtained are preserved at 3° C., with a photoperiod of 8 h of light and 16 h of darkness and at a relative humidity of 70 to 80%.

According to other features:

for long storage, the starting material is *Ephestia kuhniella* eggs aged from 0 to 24 h, the duration of the incubation period being from 24 h at 20° C. and the duration of the induction period being from 40 to 80 days at a continuous or alternating temperature comprised between about 5° and 15° C.;

for the short storage, the starting material is *Ephestia kuhniella* eggs aged about 72 h, the duration of the incubation period at 20° C. of the parasitised eggs being 96 h and the duration of the induction period being about 7 days at a temperature below 15° C.;

the prior conditioning of the *Ephestia kuhniella* eggs consists of killing them with ultraviolet light or cold and, if necessary making them stand at a temperature of 3° C. for a period less than 14 days;

the *Ephestia kuhniella* eggs are parasitised by exposing them to Trichogramma raised at 20° C. with a photoperiod of 16 h of light and 8 h of darkness, fed and freshly emerged, for a period of about 4 h.

BRIEF DESCRIPTION OF THE DRAWINGS

Other features and advantages of the invention will emerge more clearly from the description which follows, considered in association with the accompanying drawings in which.

DESCRIPTION OF A PREFERRED EMBODIMENT

Figure 1:
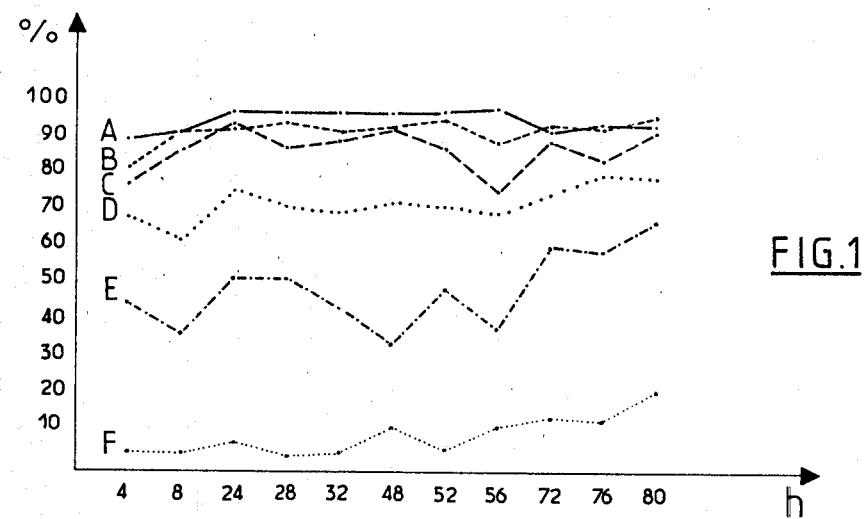
FIG. 1 is a graph indicating the percentage of emergences as a function of the age of the *Ephestia kuhnellia* eggs, of the durations of storage at 3° C. and of the dwell conditions before induction.

As mentioned above, the present invention relates to conditioning Trichogramma by cold so that it is possible at any moment, starting from batches of these Entomophages stored from 1 to 12 months at 3° C. for long storage or from 0 to 45 days for the short storage, to take specimens of parasitised eggs which give a hatching ratio, a fertility, a longevity, a percentage of winged individuals and a sex-ratio little different from those of unstored individuals.

In the case of long storage, the invention consists, on the one hand, of combining at the optimum level all the factors which facilitate the induction of an arrest in development, for example, nourishment, chronology of the progeniture, the embryonic age, the conditioning of the egg by cold and ultraviolet lights, the abiotic breeding conditions of the host, the conditions of parental generation and the laying period, namely, temperature, light, humidity, as well as the pre-imaginal development of the parasite, the age of the parasite before entering into the induction stage, the chonology of descendence, the life span without the host, the feeding of the parents and the non-superparasitism of these oophages.

The method according to the invention consists on the other hand, of reinforcing, and of prolonging the induction stage beyond the start of arrest of development observed. This reinforcement enables finally the elimination completely of the diapause and its replacement by a quiescence where the return to favourable conditions initiates the development into nymphae and then into the adult.

In accordance with the invention, eggs aged from 0 to 24 h are used killed by ultraviolet light or by cold, derived from *Ephestia kuhniella* females having already had preferably a population of descendants and emergences of larvae which may or may not have undergone cold storage. In such eggs, which have dwelt less than 14 days at 3° C.,the parasitism is carried out after feeding on honey by primipar adults raised between 20° and 23° C., aged for some hours and for a period of 4 to 24 h, without superparasitimsm and under abiotic conditions around 20° C. with a photoperiod of 8 h of light and 16 h of darkness at 70% relative humidity. It is to be noted that contrary to the known technique which tends to multiply the Trichogramma in the ratio 1 to 5 at the maximum from one generation to the next and with a high superparasitism, it is possible according to the invention to achieve a ratio 1 to 15 with a very marked tendency for monoparasitism and a sex-ratio as well as an optimum fertility for the descendence obtained.

The thus parasitised eggs are left to incubate for 24 h at 20° C., with a photoperiod of 8 h of light and 16 h of darkness, at a relative humidity of 70%. The end of incubation, of larval development, as well as a part of the blocking at the end of the larval stage is carried out at alternated or constant temperatures below 15° C. and higher than or equal to 5° C., for example 14° C., for a strain called "strain 16" (which will be defined below), a photoperiod of 8 h of light and 16 h of darkness, or again a thermoperiod of 5° to 12° C., with a photoperiod of 8 h of light at 12° C. and 16 h of darkness at 5° C., and a high relative humidity of 70 to 80% for 40 to 80 days. Storage then takes place at 3° C. under conditions of a photoperiod of 8 h of light, 16 h of darkness and a relative humidity of 70 to 80%, for 3 to 12 months without appreciable lowering of the biotic potential. The emergence ratio of the adults after weakening between 23° and 25° C. is close to 95% for the period of storage of 3 to 6 months and 90% for periods of storage of 6 months to 1 year. The emergence delays of the order of 8 days at 25° C. and 13.5 days at 20° C. for 3 month storage increase, as a function of the duration of conservation in the cold, from 1 to 3 days. The average fertility per isolated female is of the order of 75 eggs, the average longevity 16 days and the sex-ratio more than 2 females per 1 male.

Storages of short duration, of the order of 1 month, can also be obtained by resorting to *Ephestia kuhniella* eggs having for example 72 h, put to incubate after parasitism for 96 h at 20° C. before suitable induction such as 14° C. with a photoperiod of 8 h for 7 days in the case of the strain 16.

In the case of short storage, it is possible to reach relatively long developments without storage at 3° C. by developing the Trichogramma on eggs of *Ephestia kuhniella* aged 72 h, for example, at threshold-temperatures of 15° to 16° C., after staying 96 h at 20° C. (storage of 28 days) or 6 to 8 days at 25° C. (storage of 4 to 20 days). The latter conditioning ends in a generalised emergence in the several hours which follow the removal of the parasitised eggs from the cold at 15°–16° C. and which is synchronised with the climatology of the place of release.

The invention is completed by the exploitation of a so-called $F_1$ effect of considerable reinforcement of the biotic potential of the descendants of the diapausants. The latter show, in fact, with respect to their parents, a fertility and a longevity which is almost double and an increased activity of seeking the host. The possibility of obtaining both diapausants still active after one year of storage and the discovery of considerable potentialities in their descendants permit the use for releases into open fields of these two types of Trichogramma with, for diapausants, all the facilities of transportation and maintenance procured by the cold system. Government of the diapause is besides sufficiently improved for it to be possible to ensure during the whole of its development the control of the quality of the Trichogramma produced and the detection of the diapause by a simple and rapid test. It should be added that it is necessary to follow a generation in diapause by one generation, and preferably two generations, of continuous development, under unretarded life conditions, if it is desired to again introduce the diapause.

The present invention thus enables all the necessary elements to be available, on the level of practical use as a biological control, the cumulation of the daily production of Trichogramma, their preservation for more than a year, for their reutilisation either as such, or after reawakening, either by using the increased potential of their descendants, or as inoculums for parasitism of fresh host eggs. The exploitation of such an arrest hence confers a great flexibility on this type of biological control.

POSSIBILITIES OF INDUSTRIAL APPLICATION

The following examples, given by way of illustration but which are in no way limiting, will enable the scope and interest of the invention to be better grasped.

EXAMPLE 1

Effect of the Host Egg

This test was carried out in order to check what is the most favorable *Ephestia kuhniella* embryonic stage, for the development of the rapid type, of the quiescent type or of the diapause type of Trichogramma. The investigations of DAUMAL and Collaborators (1974) show that the stage sensitive to low temperatures of *Ephestia kuhniella* is from 0 to 17 h and the more resistant stage is at 72 h of embryonic development at 20° C. The tests have borne on these stages with respect to the development of Trichogramma.

For carrying out this test, two batches of 55 plates were arranged which were parasitised by Trichogramma at 20° C. for 1 h, the first batch being constituted by eggs aged 0 to 17 h, the second batch was constituted by eggs aged 72 h. Each batch was divided in turn into 11 elementary portions which were arranged at 20° C. with a photoperiod of 16 h of light and 8 h of darkness. An elementary portion including 5 plates was withdrawn every 4 h to be placed at the induction temperature. The latter was done at a temperature slightly above 15° C., which enabled a portion of the population to continue its development. No storage followed at 3° C. and the whole of the test was carried out at 70% relative humidity.

The results of this test are summarised in the graph of FIG. 1 where there are ploted a abscissae the dwell time in hours, at 20° C. before induction at 15° C., and as ordinate, the percentage of emergences of individuals. On this graph, the curves F, A, B and C are given by way of reference for storage times in months at 3° C., respectively 1 month, 3 months, 6 months and 9 months. The curves E and D relate to the percentage of emergences as a function of the age of the eggs, respectively from 0 to 17 h and 72 h.

From the curves D and E, there appears a great difference between the emergence ratio of the two series of ages of the host. It seems that the eggs of 72 h are the best for a continuous development at critical temperatures. They constitute, on the other hand, as a corollary, medium conditions very unfavorable to the diapause since the Trichogramma develop beyond the stage capable of being stored at 3° C. Conversely, the eggs from 0 to 17 h seem the most favorable for the diapause, particularly for incubation periods of 4 to 56 h before induction.

It was also sought to verify the influence of the various times of incubation at an induction temperature slightly below 15° C., namely 14° C. for hosts of 0 to 17 h for an induction period of 40 days and for storage periods in the cold at 3° C. of 1, 3, 6 and 9 months. It is seen from the graph below that it is after three months storage that the ratio of emergences is the best, namely 98%. It was still 90% after 9 months. At one month storage at 3° C., the emergence ratio was very low, mostly less than 10%.

It results from these tests that the emergence ratio depends highly significantly on the stage of development before induction and the duration of storage in the cold. It is however to be noted that the series which have incubated more than 52 h at 20° C. before induction had a low emergence percentage, of the order of 1 to 2% at the end of induction.

For notably long storage, it is hence advantageous to use eggs of 0 to 24 h, killed by ultraviolet rays or by cold and derived from females of Ephestia kuhniella which have already had preferably a population of descendants and larvae emergences which may or may not have been subjected to cold storage.

EXAMPLE II

Table 1 below summarises the average fertility ratios and the percentage of hatchings per female which have or have not undergone a storage in the cold before parasitism.

TABLE I

|  | Days of storage of the eggs |  | Storage of the parasites at 3° C. (time in days) | | | |
|---|---|---|---|---|---|---|
|  |  |  | 0 d | 30 d | 90 d | 180 d |
| Stored Ephestia (caterpillars) | 0 | Aver. fertil./female | 24.26 | 19.2 | 25.4 | 20.46 |
|  |  | % hatchings | 8.24 | 15.27 | 97.11 | 98.69 |
|  |  | Aver. fertil./female | 31 | 29 | 25.6 | 22.46 |
|  |  | % hatchings | 8.6 | 8.73 | 99.21 | 98.51 |
|  |  | Aver. fertil./female | 19.86 | 9.73 | 13.3 |  |
|  |  | % hatchings | 2.41 | 30.82 | 94.5 |  |
|  |  | Aver. fertil./female | 7.06 | 7.2 | 6.33 |  |
|  |  | % hatchings | 0 | 14.81 | 78.94 |  |
| Unstored Ephestia (caterpillars) |  | Aver. fertil./female | 19.93 | 26 | 22.2 | 13.6 |
|  |  | % hatchings | 3.01 | 5.62 | 98.49 | 99.01 |
|  |  | Aver. fertil./female | 29 | 27.93 | 29.13 | 24.8 |
|  |  | % hatchings | 7.56 | 6.68 | 99.77 | 99.46 |
|  |  | Aver. fertil./female | 16.86 | 19.86 | 13.13 |  |
|  |  | % hatchings | 8.69 | 18.12 | 95.93 |  |
|  |  | Aver. fertil./female | 10.13 | 6.4 | 5.06 |  |
|  |  | % hatchings | 0.65 | 8.33 | 89.47 |  |

It is observed that the most effective parasitism takes place in eggs which have stood less than 14 days at 3° C.

EXAMPLE 3

It was desired to check whether the breeding of the parents at various temperatures could have an effect on the diapause of the progeniture induced by different temperatures and photoperiods as a function of the different induction times. It was also desired to determine the possible influence of the method of sticking the eggs with water or with glue on the quality of this diapause.

(a) Preparation of the Inoculums (Parent Generation)

3 Batches of 96 tubes each containing an inoculum of 100 parasitiesed eggs in 24 h at 23° C., was arranged, one at 15° C., the other at 20°–23° C. and the third batch at 23°–27° C.

(b) Preparation of the Host Eggs for the Daughter Generation

At the moment of emergence of the parental adults two plates of 500 eggs treated with ultraviolet lights are introduced into each tube, one comprising eggs stuck with water, the other comprising eggs stuck by means of a 30% aqueous solution of gum arabic.

(c) Mode of Induction

Half of each batch is placed at 13.5° C. and the other half at 10° C. At each of these temperatures, the stock is in its turn divided into two portions: one is subjected to the photoperiod of 8 h of light—16 h of darkness and the other to 16 h of light—8 h of darkness, each for half until greying, the other until greying plus 2 weeks. In this way, 48 elementary batches of 12 plates were available which were stored at 3° C.

(d) Method of Storage

By elementary treatment, 4 plates were stored for 1 month, 4 plates for 3 months and 4 plates for 6 months. After storage, reactivation at 23°–27° C. was carried out and the emergence ratio was calculated on 100 eggs. During all the phases of these tests, the relative humidity was maintained at 70%.

It is first observed that the breeding of the moldave strain of *Trichogramma evanescens* at 15° C. results in a considerable percentage of diapausants and, for this reason, the batch intended to produce parental imagos at this temperature was removed.

It ensues from this test that the mode of sticking does not interfere with the emergence ratio, whether this factor is considered separately or in interaction with the other factors. The breeding temperature of the parents does not show any significant effect separately, but it has on the other hand an interaction in the daughter generation. This interaction is reinforced moreover with an interaction of the third order which is highly significant with the induction temperature and significant with the induction photoperiod. The latter factor has moreover, still associated with the breeding temperature of the parents, an interaction of the third order with the duration of storage at 3° C.

The most influential factors are finally, on the one hand, the conditions of induction of the daughter generation, photo-period, duration and temperature of induction and on the other hand, the storage method at 3° C., separately and in interaction with the temperature and the duration of induction. The effect of the induction temperature is, moreover, reinforced in a highly significant manner by the photoperiod and the duration of induction.

EXAMPLE 4

The test which follows was carried out for the purpose of checking whether it is possible to detect a difference in the diapause quality connected with two induction temperatures very close to one another. In addition, two exposure periods of the parasites to their host were carried out, one of short duration (4 h), which corresponds to a continuous production of parasitised *Ephestia kuhniella* eggs, the other of long duration (24 h), closer to the normal production of Trichogramma. In the first type, superparasitism was almost nonexistant. In the second type, it was more frequent.

Experimental Device

132 Plates of *Ephestia kuhniella* eggs passed through ultraviolet rays were exposed to Trichogramma, 62 plates were withdrawn after 4 h of parasitism, the others after 24 h. These two series of plates parasitised in this manner were placed at a temperature slightly below 15° C., with a photoperiod of 8 h of light-16 h of darkness, at 70% relative humidity. Each day, a batch of 6 plates of each series were passed at 13.5° C., with a photoperiod of 8 h of light-16 h of darkness and at 70% relative humidity, until darkening of the eggs more than 10 days. These plates were then placed at 3° C. and they were withdrawn after 1 month, 3 months and 6 months' storage respectively. Reactivation was carried out at 23°–27° C., at 70% relative humidity. After awakening for each elementary treatment, 5 females were isolated in order to know their fertility in 7 days.

Figure 2:
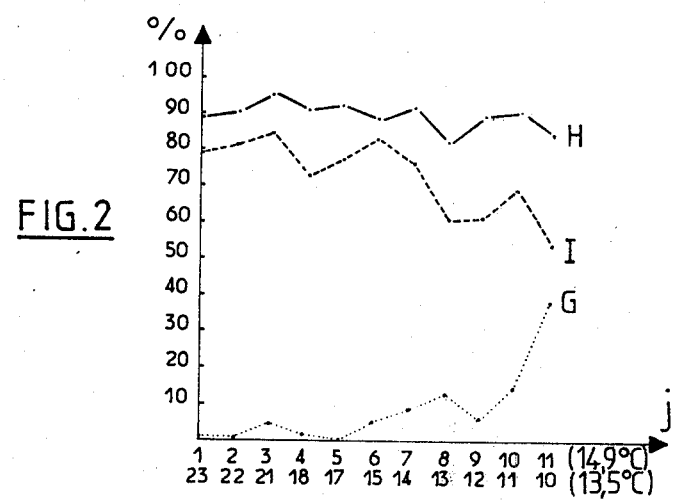
FIGS. 2 and 3 are graphs indicating the percentage of emergences as a function of the induction period, respectively for parasitisms and consequently of incubations of 0 to 4 h and of 0 to 24 h at 20° C. of the parasitised eggs.
Figure 3:
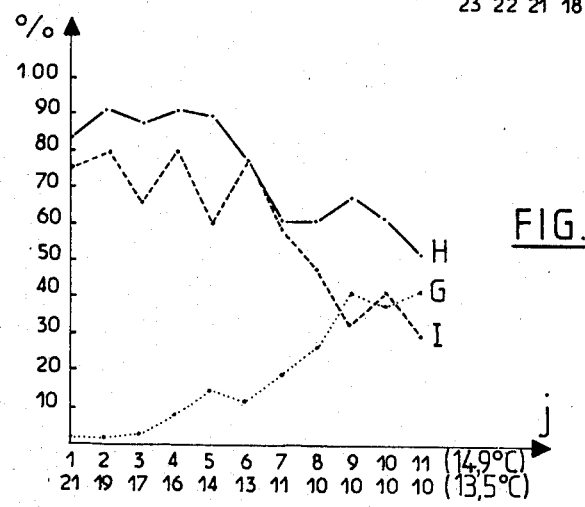

The results of these tests are indicated in the graphs of FIGS. 2 and 3 where the duration of induction in days is plotted as abscissae, on two scales respectively at 14.9° C. and 13.5° C., and as ordinates the percentage of emergences of individuals. On these graphs, the curves G, H and I correspond respectively to 1 month, 3 months and 6 months storage at 3° C. It results from these tests that there exists a highly significant difference between the two periods of parasitism, that of 4 h leading in almost all cases to a better diapause. These differences may be attributed either to the fact of a superparasitism which is greater after 24 h exposure of the *Ephestia kuhniella* eggs to Trichogramma, this superparasitism leading to retarding the induction of a diapause, or to a better competence of the first eggs of the parasite for the diapause.

It was observable in addition that, in the case where there was no superparasitism and for longer induction periods, o the order of 40 days, it was possible to obtain a very good percentage (greater than 95%) of emergence in the case of 24 h of parasitism.

EXAMPLE 5

The object of the tests summarised in Tables II and III which follow is to show that it is possible to reach a ratio 1 to 15 with a marked tendency for monoparasitism and an optimum sex-ratio as well as a fertility for descendants from *Ephestia kuhniella* eggs parasitised by Trichogramma.

TABLE II

| 20° C. 70% relative humidity | Number of host eggs/female | | | | | |
|---|---|---|---|---|---|---|
| | 11 | 2 | 5 | 10 | 20 | 40 |
| % of females which lay from the 1st to 20th h. | 99 | 4 | 7 | 20 | 40 | 88 |
| % of parasitised whole dark eggs in 24 hours | 29.16 | 40.19 | 42.68 | 66.52 | 77.8 | 73.5 |
| % of hatched parasitised eggs | 78.57 | 65.8 | 69.5 | 88.12 | 93.8 | 98 |
| Sex-ratio $\frac{\text{Number of males}}{\text{Number of females}}$ | 2 | 1 | 0.72 | 0.41 | 0.2 | 0.2 |
| Average fertility per female | | | | 40.5 | 54.65 | 59 | 62.16 |
| Period of development | 17 | 17 | 16 | 15 + 6 | 15 + 2 | 15 |

TABLE II-continued

| 20° C. 70% relative humidity | Number of host eggs/female | | | | | |
|---|---|---|---|---|---|---|
| | 1 | 2 | 5 | 10 | 20 | 40 |
| in D (first emergences) | | | | hours | hours | |

TABLE III

| 0-24 h parasitism at 20° C., 70% R.H. | Number of eggs | | | | |
|---|---|---|---|---|---|
| | parasitised | collapsed parasitised | collapsed whites | collapsed yellows | Number emerged |
| 10 females - 10 eggs | 6 | | 4 | | 6 |
| | 2 | | 6 | | 2 |
| | 5 | | 3 | 2 | 3 |
| | 1 | | 7 | 2 | 0 |
| | 0 | | 9 | 1 | |
| 10 females - 20 eggs | 2 | | 17 | 1 | 2 |
| | 14 | 2 | 6 | | 9 |
| | 15 | | 5 | | 11 |
| | 6 | 3 | 11 | | 2 |
| | 4 | 2 | 10 | 4 | 3 |
| 10 females - 50 eggs | 28 | 8 | 12 | 4 | 17 |
| | 13 | 6 | 20 | 13 | 9 |
| | 18 | 3 | 21 | 6 | 14 |
| | 23 | 5 | 16 | 3 | 16 |
| | 23 | 9 | 17 | | 17 |
| 10 females - 100 eggs | 51 | 11 | 21 | 8 | 39 |
| | 50 | 10 | 30 | 4 | 39 |
| | 77 | 2 | 11 | | 75 |
| | 60 | 15 | 27 | | 49 |
| | 82 | 2 | 18 | 2 | 80 |
| 10 females - 200 eggs | 156 | 4 | 56 | | 148 |
| | 150 | 1 | ~35 | | 138 |
| | 197 | 2 | ~30 | | 190 |
| | 104 | 2 | ~42 | | 92 |
| | 128 | 4 | ~28 | | 122 |
| 10 females - 400 eggs | 285 | 1 | white eggs still in good condition | | 279 |
| | 296 | | | | 288 |
| | 319 | | | | 316 |
| | 292 | | | | 287 |
| | 278 | | | | 272 |

EXAMPLE 6

$F_1$ Effect

The purpose of this example is to show the influence of the awakening conditions on the fertility of the diapausing females and that of the diapause on the fertilities of the descendents, the treatment comprising notably an induction period of 30 days at a temperature comprised between 12° and 15° C. The awakening conditions, the effect of the diapause on the daughter descendents compared with two controls, one originating from the initial population, the other from descendents of this control, pertain for each series to 25 females. The fertilities were determined on the second day by changing the plates, then the tenth day and, then, from week to week. The sex-ratio was also determined. From the tenth day, dissections were carried out on 300 parasitised eggs every two days to know the distribution of the various stages in the population.

(a) Distribution of the stages at induction temperature (from 10th to 30th day)

1st to 10th day: all the individuals were in the final stage of 3rd prenymphal larval stage. The eggs were of a medium grey color.
2nd to 14th day: appearance of 17 hyaline nymphs
3rd to 16th day: appearance of 20 hyaline nymphs
4th to 19th day: appearance of 13 hyaline nymphs appearance of 7 nymphs with red eyes
5th to 22nd day: appearance of 13 hyaline nymphs appearance of 7 nymphs with red eyes
6th to 25th day: appearance of 14 hyaline nymphs appearance of 2 nymphs with red eyes appearance of 2 nymphs at the very beginning of sclerification.
7th to 30th day: appearance of 18 hyaline nymphs appearance of 4 nymphs with red eyes appearance of 2 nymphs distinctly sclerified.

(b) The percentages of emergences were, for the three types of awakening R1, R2, R3 (see below) respectively 61.7, 63.8 and 54.5%. The appearance of the first adults takes place 10 days after the emergence of the parasitised eggs from their cold storage. The sex-ratio was high: about 1 male per 2 females, whilst for the generation $F_1$, it was 1 male per 6 females (see below).

The spread of emergences take place practically over 4 days and 85% of the emergences took place in two days.

The modes of awakening are summarised as follows:
$R_1$: awakening at 23°-27° C.
$R_2$: awakening at 20° C., for 3 days, then 23°-27° C.
$R_3$: awakening at 15° C., for 3 days, then 23°-27° C.
$F_1$: daughter generation bred at 23°-27° C.
T: control bred at 20° C.
$F_1T$: generation of the control bred at 23°-27° C.

TABLE IV

| | Fertility in average number of eggs laid per female | | |
|---|---|---|---|
| | total | 0-2 days | 0-10 days |
| $R_1$ | 81.6 | 28.2 | 65.6 |
| $R_2$ | 80.8 | 28.2 | 65.8 |
| $R_3$ | 87.6 | 31.6 | 66.7 |
| $F_1$ | 152.1 | 56.8 | 112.6 |
| T | 75 | 28.5 | 57.4 |
| $F_1T$ | 124.7 | 44.6 | 93.8 |

Longevity

To the 6 treatments examined for fertility, corresponds the average longevities given in the following Table V:

TABLE V

| | Average longevity in days |
|---|---|
| $R_1$ | 19.44 |
| $R_2$ | 16.72 |
| $R_3$ | 19.52 |
| $F_1$ | 23.56 |
| T | 22.76 |
| $F_1T$ | 21.84 |

The method according to the invention enables mass production of Trichogramma enabling notably the storage of the oophage produced for a relatively long time, which permits the distribution of the site of production in the field. The diapause of the individuals is precisely a state which permits at the same time storage in the cold, use of the cold chain for transportation as well as the accumulation of daily, monthly and even annual productions. The production of the Trichogramma permits notably the putting into practice of the biological control in the form of inondative and seasonal releases, in particular in corn fields within the scope of combatting the Ostrinian nubilalis hubner pyralis of corn.

As mentioned above, a "strain 16" of Trichogramma, especially adapted by Applicant, is particularly suitable in the practising of the above-described method.

In accordance with the present invention, the strain no 16 is a chalcidian hymenopterous insect of the Trichogrammatidae family modified and adapted for the destruction of Ostrinia nubilalis eggs (corn meal moth). Trichogramma evanescens was described in 1833 by Westwood J. O. (locality of the type: England), it relates to a parasitoid whose larvae live at the expense of lepidotera eggs.

The species are redescribed morphologically by Nagarkatti (S) and Nagaraja (H) in 1971.

As mentioned above, trichogramma are already employed in biological control in numerous countries, but never has an active strain which is very well defined such as strain no. 16 been obtained. The latter was discovered in Moldavia (U.R.S.S.) by Jean VOEGELE in Ostrinia nubilalis eggs in corn. Applicant conducted breeding, by means of Ephestia kuhniella eggs so as to select the most fertile individuals and to obtain total inbreeding. Hence it does not concern a natural population but a renewable batch of all identical individuals. This strain No. 16 is unique and is constituted by trichogramme maidis which is included in the generic group of trichogramme evanescens.

Below are given the quantitative identification characters of this strain No. 16 (abiotic conditions: 25° C., 70% R.H., 16 h of daylight per day).

(1) Fertility

It is expressed by the fertility (number of adult offspring obtained)

|  | Fertilized females | Virgin females |
|---|---|---|
| 3 first days of laying | 33.53 ± 2.02 | 46.47 ± 3.27 |
| 5 first days of laying | 44.67 ± 2.58 | 46.56 ± 3.62 |
| 7 first days of laying | 51.87 ± 2.31 | 61.53 ± 3.54 |

(2) Sex-ratio (percentage of females)

progeniture coming from the 3 first days of laying: 0.69±0.04
progeniture coming from the 5 first days of laying: 0.68±0.02
progeniture coming from the 7 first days of alying: 0.64±0.03
Total sex-ratio=0.60

(3) Emergence percentage 82.0%

(4) Longevity

Longevity of fertilized females: 10.4±0.3 day
Percentage of individuals dead before 8 days:
Virgin females: 0%
Fertilized females: 6.2%
Males: 81.2%

(5) Sterility Percentage

Females: 2.97% Males: 7.69%

(6) Standard seeking capacity for the host (E. kuhniella)

|  | Females | Males |
|---|---|---|
| Imo:Mobility Index | 1.6 | 0.4 |
| Icr:Search Capacity Index | 10.7 | 0.9 |
| Iat:Attractivity Index | 9.1 | 0.5 |

Below are given the qualitative identification characters.

By electrophoresis, certain enzymes have been characterised: esterases, malate-dehydrogenases and tetrazolium-oxidases. If the two latter do not occur in the strain in a particular state, the esterases enable, on the other hand, precise identification.

No polymorphism was detected. Five strips corresponding to 5 locus, had electrophoretic mobilities of 0.10; 0.22; 0.28; 0.50 and 0.53. The first and the two latter were the most intense.

In 28 strains analysed, including 2 coming from strain no. 16 of corn crops, none possessed such esterasic properties.

It results from the data above that by means of all these characteristics, it is not possible to confuse strain no. 16, on the one hand, with any one of the 150 lines known and, on the other hand, with a natural population.

Strain no 16 of trichogramma applicable to the method according to the invention intended for the control of flour moth is unique and recognizable.

The method according to the invention enables the putting into practice of a method of biological control of plant pest lepidoptera, notably flour moth, by means of the oophage parasitic insect. By this method of control, in which an at least annual spreading in the field of host eggs of the oophage parasite on the plants to be protected is carried out, a single spreading is advantageously effected, at the period corresponding to the beginning of laying of the lepidoptera, of a measured mixture of eggs-hosts which has undergone conditioning so that some, a first wave, include the oophage in the last stage of evolution and others, a second wave, include the oophage in the pre-nymph stage, by means of which imagos coming from the eggs of the first wave emerge after 1 to 2 days and those coming from the second wave emerge after 15 to 20 days.

It is well understood that the present invention has only been described and illustrated purely by way of explanation but not in any limiting manner and that it would be possible to introduce any useful modification therein within the field of technical equivalents without departing from its scope.

We claim:

1. Method of conditioning and preserving insect oophage parasites eggs, intended notably for biological control of certain plant pests, including parasitage of an egg-host and preservation in the cold, said method comprising the steps of:
starting with Lepidoptera eggs of foodstuffs, in particular of Ephestia kuhniella, parasitizing these eggs with adult Trichogramma, subjecting the thus parasitized eggs to an incubation period of at least 24 h at 20° C., with a photoperiod of 8 h light and 16 h darkness and a relative humidity of 70 to 80%, subjecting the thus incubated eggs to an induction period of about 6 to 80 days, at a temperature below 15° C. with a photoperiod of 8 h light and 16 h darkness, and a relative humidity of about 70%, then preserving the eggs thus obtained at 3° C., with a photoperiod of 8 h light and 16 h darkness and at a relative humidity of 70 to 80%.

2. Method according to claim 1, wherein for long storage, the starting material is Ephestia kuhniella eggs aged from 0 to 24 h, the duration of the incubation period of the parasite being 24 h at 20° C. and the duration of the induction period being 40 to 80 days at a temperature comprised between about 5° and 15° C.

3. Method according to claim 1, wherein for short storage, the starting material is *Ephestia kuhniella* eggs aged about 72 h, the duration of the incubation period being 96 h at 20° C. and the duration of the induction period being 6 to 8 days at a temperature below 15° C.

4. Method according to claim 1, wherein the *Ephestia kuhniella* eggs are preconditioned prior to said parasitizing by killing them with ultraviolet rays and if necessary keeping them at a temperature of 3° C. for a period less than 14 days.

5. Method according to claim 1, wherein the *Ephestia kuhniella* eggs are preconditioned prior to said parasitizing by killing them by cold and, if necessary keeping them at a temperature of 3° C. for a period less than 14 days.

6. Method according to claim 1, in which the *Ephestia kuhniella* eggs are parasitised by exposing them to Trichogramma raised at 20° C. with a photoperiod of 16 h light and 8 h darkness, nourished and freshly emerged during a period of about 4 to 24 h.

7. Method according to claim 1, wherein the awakening of the eggs preserved at 3° C. is carried out at a temperature comprised between 23° and 27° C., with if necessary a plateau of about three days at 20° C.

8. Method according to claim 1, wherein there is utilized more particularly, for the biological control the second generation of Trichogramma coming from egg-hosts preserved at 3° C.

* * * * *